United States Patent
Masuda et al.

(10) Patent No.: US 11,135,297 B2
(45) Date of Patent: Oct. 5, 2021

(54) EXTERNAL-USE COMPOSITION PRODUCING FOAMED STATE UPON USE

(71) Applicant: POLA PHARMA INC., Tokyo (JP)

(72) Inventors: Takaaki Masuda, Yokohama (JP); Hirokazu Kobayashi, Yokohama (JP)

(73) Assignee: POLA PHARMA INC., Tokyo (JP)

( * ) Notice: Subject to any disclaimer, the term of this patent is extended or adjusted under 35 U.S.C. 154(b) by 0 days.

(21) Appl. No.: 14/902,924

(22) PCT Filed: Jul. 10, 2014

(86) PCT No.: PCT/JP2014/068407
§ 371 (c)(1),
(2) Date: Jan. 5, 2016

(87) PCT Pub. No.: WO2015/005419
PCT Pub. Date: Jan. 15, 2015

(65) Prior Publication Data
US 2016/0136278 A1    May 19, 2016

(30) Foreign Application Priority Data
Jul. 11, 2013   (JP) .............................. JP2013-157134

(51) Int. Cl.
| | |
|---|---|
| *A61K 47/22* | (2006.01) |
| *A61K 9/12* | (2006.01) |
| *A61K 9/00* | (2006.01) |
| *A61K 47/14* | (2017.01) |
| *A61K 31/4015* | (2006.01) |
| *A61K 45/06* | (2006.01) |
| *A61K 31/21* | (2006.01) |
| *A61K 31/137* | (2006.01) |
| *A61K 31/355* | (2006.01) |
| *A61K 31/381* | (2006.01) |
| *A61K 31/439* | (2006.01) |
| *A61K 31/57* | (2006.01) |
| *A61K 31/58* | (2006.01) |
| *A61K 31/593* | (2006.01) |
| *A61K 31/727* | (2006.01) |
| *B65B 3/04* | (2006.01) |
| *B65D 83/14* | (2006.01) |

(52) U.S. Cl.
CPC ............ *A61K 47/22* (2013.01); *A61K 9/0014* (2013.01); *A61K 9/122* (2013.01); *A61K 31/137* (2013.01); *A61K 31/21* (2013.01); *A61K 31/355* (2013.01); *A61K 31/381* (2013.01); *A61K 31/4015* (2013.01); *A61K 31/439* (2013.01); *A61K 31/57* (2013.01); *A61K 31/58* (2013.01); *A61K 31/593* (2013.01); *A61K 31/727* (2013.01); *A61K 45/06* (2013.01); *A61K 47/14* (2013.01); *B65B 3/04* (2013.01); *B65D 83/752* (2013.01)

(58) Field of Classification Search
CPC .... A61K 31/355; A61K 31/137; A61K 9/122; A61K 31/593; A61K 47/14; A61K 9/0014; A61K 31/58; A61K 31/727; A61K 47/22; A61K 31/57; A61K 31/4015; A61K 31/439; A61K 45/06; A61K 31/21; A61K 31/381; B65B 3/04; B65D 83/752; A61P 37/06; A61P 29/00; A61P 3/02; A61P 31/10; A61P 31/00
See application file for complete search history.

(56) References Cited

U.S. PATENT DOCUMENTS

| | | | |
|---|---|---|---|
| 6,576,633 B1 * | 6/2003 | Young .................... | A01N 43/90 514/241 |
| 2004/0241099 A1 | 12/2004 | Popp et al. | |
| 2005/0220743 A1 * | 10/2005 | Nojiri .................... | A61K 8/046 424/70.1 |
| 2006/0034779 A1 | 2/2006 | Arkin et al. | |
| 2006/0275218 A1 | 12/2006 | Tamarkin et al. | |
| 2007/0020213 A1 | 1/2007 | Tamarkin et al. | |
| 2007/0059253 A1 | 3/2007 | Popp et al. | |
| 2014/0200203 A1 * | 7/2014 | Evers ..................... | A61P 29/00 514/172 |

FOREIGN PATENT DOCUMENTS

| | | | |
|---|---|---|---|
| EP | 1839643 A1 | 10/2007 | |
| JP | 61210023 A | * 9/1986 | |
| JP | 8-291050 A | 11/1996 | |
| JP | 10-158122 A | 6/1998 | |
| JP | 2000-256138 A | 9/2000 | |
| JP | 2002-161020 A | 6/2002 | |
| JP | 2003-055160 A | 2/2003 | |
| JP | 2003-268400 A | 9/2003 | |
| JP | 2006-137722 A | 6/2006 | |
| JP | 2007-500235 A | 1/2007 | |
| JP | 2007-314494 A | 12/2007 | |
| JP | 2008-540508 A | 11/2008 | |
| WO | WO 2006/129161 A2 | 12/2006 | |

OTHER PUBLICATIONS

International Search Report for International Application No. PCT/JP2014/068407, dated Sep. 16, 2014.
Extended European Search Report issued in corresponding European Patent Application No. 14822508.9, dated Nov. 30, 2016.

\* cited by examiner

*Primary Examiner* — Lezah Roberts
(74) *Attorney, Agent, or Firm* — Knobbe, Martens, Olson & Bear LLP

(57) ABSTRACT

Compositions having an increased amount of an effective component retained in the composition for a pump foamer are provided. A composition for external use is described which contains: 1) an N-alkyl-2-pyrrolidone and/or a diester carbonate; and 2) a surfactant. The composition is in a foam state upon use.

11 Claims, No Drawings

EXTERNAL-USE COMPOSITION PRODUCING FOAMED STATE UPON USE

CROSS-REFERENCE TO RELATED APPLICATIONS

This application is the U.S. National Phase under 35 U.S.C. § 371 of International Application PCT/JP2014/068407, filed Jul. 10, 2014, which claims priority to JP 2013-157134, filed Jul. 11, 2013.

TECHNICAL FIELD

The present invention relates to a composition for external use, more specifically, a composition for external use producing a foamed state upon use.

BACKGROUND ART

External pharmaceutical formulations can be roughly divided into 5 types of formulations: lotion formulations, ointment formulations, cream formulations, spray aerosol formulations, and foam aerosol formulations. Among these, spray aerosol formulations and foam aerosol formulations are attracting attention since these can be uniformly and widely administered to the affected area while physical stimulation to the area is reduced (see, for example, Patent Document 1). However, on the other hand, it is already known that the gas composition per se for spraying of the aerosol is highly likely to irritate the skin (see, for example, Patent Document 2). There is a means for avoiding this, wherein aerosol such as foam is formed using a pump foamer, without filling of a foaming gas. In terms of the foam formed using a pump foamer, the foam-forming ability is often deteriorated due to a solvent component or a polyol, so that only an extremely limited variety of prescriptions are applicable. In other words, development of a means for increasing the amount of an effective component retained in a composition for a pump foamer has been demanded.

On the other hand, solvents such as propylene carbonate have already been used in foaming aerosols (see, for example, Patent Document 3 and Patent Document 4), but they have never been used in compositions for pump foamers. This is thought to be due to the fact that the foam-forming abilities of pump foamers are lower than those of foam-forming gases.

Compositions for external use containing: 1) an N-alkyl-2-pyrrolidone and/or a diester carbonate; and 2) a surfactant; which compositions being in a foam state upon use and to be used for a pump foamer, have been totally unknown.

PRIOR ART DOCUMENTS

Patent Documents

Patent Document 1: JP 2007-314494 A
Patent Document 2: JP 10-158122 A
Patent Document 3: JP 2006-137722 A
Patent Document 4: JP 08-291050 A

SUMMARY OF INVENTION

Technical Problem

The present invention was made under such circumstances, and an object of the present invention is to provide a means for increasing the amount of an effective component retained in a composition for a pump foamer.

Solution to Problem

In view of the above-described circumstances, the present inventors intensively studied in order to find a means for increasing the amount of an effective component retained in a composition for a pump foamer, and, as a result, discovered that a composition for external use containing: 1) an N-alkyl-2-pyrrolidone and/or a diester carbonate; and 2) a surfactant; which composition is in a foam state upon use and to be used for a pump foamer, has such a property, thereby completing the present invention. That is, the present invention is as follows.

<1> A composition for external use comprising: 1) an N-alkyl-2-pyrrolidone and/or a diester carbonate; and 2) a surfactant, wherein the composition is in a foam state upon use.

<2> The composition for external use according to <1>, comprising: 1) an effective component; 2) an N-alkyl-2-pyrrolidone and/or a diester carbonate; and 3) a surfactant, wherein the composition is in a foam state upon use.

<3> The composition for external use according to <2>, wherein the effective component comprises one or more selected from the group consisting of vitamin A and derivatives thereof, vitamin D and derivatives thereof, vitamin E and derivatives thereof, immunosuppressants, antibiotics, antifungal agents, anti-inflammatory agents, glucocorticoid, heparin, and heparinoids.

<4> The composition for external use according to any one of <1> to <3>, wherein the N-alkyl-2-pyrrolidone comprises one or more selected from the group consisting of N-methyl-2-pyrrolidone, N-ethyl-2-pyrrolidone, N-propyl-2-pyrrolidone, and N-butyl-2-pyrrolidone.

<5> The composition for external use according to any one of <1> to <4>, wherein the diester carbonate is propylene carbonate.

<6> The composition for external use according to any one of <1> to <5>, wherein the surfactant comprises one or more selected from the group consisting of: fatty acid monoglycerides to which polyoxyethylene is optionally added; fatty acid esters of polyglycerol; sorbitan fatty acid esters to which polyoxyethylene is optionally added; alkyl or alkenyl ethers of polyoxyethylene; fatty acid diethanol amides; and polyoxyethylene castor oils which are optionally hydrogenated.

<7> The composition for external use according to any one of <1> to <6>, comprising not less than 10% by mass of alcohol.

<8> The composition for external use according to <7>, comprising not less than 15% by mass of glycerol.

<9> The composition for external use according to any one of <1> to <8>, which forms foam upon use with a pump foamer.

<10> A pharmaceutical prepared by filling the composition for external use according to any one of <2> to <9> in a pump foamer.

Advantageous Effects of Invention

According to the present invention, a means for increasing the amount of an effective component retained in a composition for a pump foamer can be provided.

DESCRIPTION OF EMBODIMENTS

<1> Effective Component as Essential Component of External Pharmaceutical Composition of Present Invention A mode of the composition for external use of the present invention is an external pharmaceutical composition comprising: 1) an effective component; 2) an N-alkyl-2-pyrrolidone and/or a diester carbonate; and 3) a surfactant; which composition is in a foam state upon use.

The pharmaceutical prepared by filling the composition for external use of the present invention in a pump foamer comprises an effective component as an essential component. The effective component which may be used in the composition for external use of the present invention is not limited as long as the component is an effective component defined as a pharmaceutical by the Pharmaceutical Affairs Law, and may be preferably selected from the following examples: vitamin A and derivatives thereof such as retinol, vitamin A acid, and tocoretinate; vitamin D and derivatives thereof such as vitamin $D_2$, vitamin $D_3$, maxacalcitol, and adapalene; vitamin E and derivatives thereof such as tocopherol and tretinoin tocoferil; immunosuppressants such as cyclosporin and tacrolimus; antibiotics such as achromycin, tetracycline, gentamycin, chloramphenicol, penicillin G, polymixin, and colistin methanesulfonate; antifungal agents such as butenafine, terbinafine, bifonazole, lanoconazole, and luliconazole; anti-inflammatory agents such as indomethacin, ketoprofen, ketotifen, nalfurafine, and suprofen; glucocorticoids such as hydrocortisone, prednisolone, dexamethasone valerate, and mometasone furancarboxylate; and heparin and heparinoids such as chondroitin-4-sulfate, chondroitin-6-sulfate, dermatan acid, and keratan acid. The content of such an effective component is not limited as long as it is in accordance with a content at which each component is commonly used, and the content is preferably about 0.001 to 10% by mass, more preferably about 0.005 to 5% by mass with respect to the total amount of the composition for external use.

The composition for external use of the present invention may be applied to diseases for which the effective component as a pharmaceutical is effective, referring to the doses and usage of conventional preparations.

<2> N-alkyl-2-pyrrolidone and Diester Carbonate as Essential Components of Composition for External Use of Present Invention The composition for external use of the present invention contains an N-alkyl-2-pyrrolidone and/or a diester carbonate. In the constitution of the present invention, these components have actions to allow dissolution of an effective component without deteriorating the foam-forming ability with a pump foamer. Only one component, or a combination of two or more components may be used. For exertion of the above-described action, the total content of the component(s) is preferably 0.5 to 10% by mass, more preferably 1 to 5% by mass with respect to the total amount of the composition for external use.

In cases where the content is too small, the action to allow dissolution of the effective component may not be sufficiently exerted, while in cases where the content is too large, the foam-forming ability may be deteriorated. Preferred examples of the alkyl group in the N-alkyl-2-pyrrolidone include methyl, ethyl, propyl, and butyl. The alkyl group is especially preferably methyl or ethyl.

As the diester carbonate, either a cyclic diester of a dihydric alcohol or a diester of two monohydric alcohols may be employed. Preferred examples of the diester carbonate include ethylene carbonate, propylene carbonate, and dicapryl carbonate.

<3> Surfactant as Essential Component of Composition for External Use of Present Invention The composition for external use of the present invention contains a surfactant as an essential component. Examples of the surfactant include nonionic surfactants, anionic surfactants, cationic surfactants, and amphoteric surfactants. Among these, nonionic surfactants are especially preferred. In particular, the surfactant is preferably selected from the group consisting of: fatty acid monoglycerides to which polyoxyethylene is optionally added; fatty acid esters of polyglycerol; sorbitan fatty acid esters to which polyoxyethylene is optionally added; alkyl or alkenyl ethers of polyoxyethylene; fatty acid diethanol amides; and polyoxyethylene castor oils which are optionally hydrogenated.

The average addition molar number of the polyoxyethylene is preferably 5 to 25.

The average addition molar number of the polyglycerol is preferably 2 to 10.

The average carbon number of the fatty acid constituting the fatty acid monoglyceride, fatty acid ester of polyglycerol, or sorbitan fatty acid ester is preferably 6 to 18, more preferably 6 to 16.

The average carbon number of the alkyl group or the alkenyl group in the alkyl or alkenyl ether of the polyoxyethylene is preferably 10 to 16.

The average carbon number of the fatty acid constituting the fatty acid diethanol amide is preferably 10 to 18, especially preferably 10 to 14.

An especially preferred mode of the surfactant is a mode using the combination of: a) a polyoxyethylene (average addition molar number, 6 to 10) fatty acid (average carbon number, 6 to 14) monoglyceride and/or a fatty acid diethanol amide; and b) a polyoxyethylene (average addition molar number, 8 to 25) alkyl ether and/or a polyoxyethylene (average addition molar number, 20 to 80) hydrogenated castor oil.

In this case, the mass ratio between a) the polyoxyethylene (average addition molar number, 6 to 10) fatty acid (average carbon number, 6 to 14) monoglyceride and/or the fatty acid diethanol amide and b) the polyoxyethylene (average addition molar number, 8 to 25) alkyl ether and/or the polyoxyethylene (average addition molar number, 20 to 80) hydrogenated castor oil is especially preferably 1:4 to 1:1 from the viewpoint of stabilizing the solubilization system. Since the composition for external use of the present invention is administered to skin that may be damaged, and may be used under conditions where no washing operation is carried out, the composition preferably does not substantially contain an anionic surfactant, cationic surfactant, or amphoteric surfactant, or acylated amino acid-based surfactant.

The content of the surfactant in the composition for external use of the present invention is preferably 0.1 to 10% by mass, more preferably 0.5 to 7% by mass with respect to the total amount of the composition for external use.

In the composition for external use of the present invention, the ratio between 2) the N-alkyl-2-pyrrolidone and/or the diester carbonate and 3) the surfactant is usually 20:1 to 1:20, preferably 15:1 to 1:15, more preferably 10:1 to 1:10 in terms of the mass ratio. By using such a surfactant, a composition for external use having favorable foam-forming ability and excellent stability can be provided. Moreover, at this content ratio, solubility of the effective component is high.

The composition for external use of the present invention contains the essential component, and is a solubilized formulation. The composition is used in a form for external use. The composition for external use of the present invention may contain, in addition to the essential component, arbitrary components for formulation that are normally used for pharmaceutical compositions. Preferred examples of such components include oils and waxes such as macadamia nut oil, avocado oil, corn oil, olive oil, rapeseed oil, sesame oil, castor oil, safflower oil, cottonseed oil, jojoba oil, coconut oil, palm oil, liquid lanolin, hydrogenated palm oil, hydrogenated oil, Japan wax, hydrogenated castor oil, beeswax, candelilla wax, carnauba wax, ibota wax, lanolin, reduced lanolin, hard lanolin, and jojoba wax; hydrocarbons such as liquid paraffin, squalane, pristane, ozocerite, paraffin, ceresin, vaseline, and microcrystalline wax; higher fatty acids such as oleic acid, isostearic acid, lauric acid, myristic acid, palmitic acid, stearic acid, behenic acid, and undecylenic acid; higher alcohols such as cetyl alcohol, stearyl alcohol, isostearyl alcohol, behenyl alcohol, octyldodecanol, myristyl alcohol, and cetostearyl alcohol; synthetic ester oils such as cetyl isooctanoate, isopropyl myristate, hexyldecyl isostearate, ethylene glycol di-2-ethyl hexanoate, neopentyl glycol dicaprate, glycerol di-2-heptyl undecanoate, glycerol tri-2-ethyl hexanoate, trimethylolpropane tri-2-ethyl hexanoate, trimethylolpropane triisostearate, and pentaneerythritol tetra-2-ethylhexanoate; chain polysiloxanes such as dimethylpolysiloxane, methylphenylpolysiloxane, and diphenylpolysiloxane; cyclic polysiloxanes such as octamethylcyclotetrasiloxane, decamethylcyclopentasiloxane, and dodecamethylcyclohexanesiloxane; oils such as silicone oils including modified polysiloxanes, for example, amino-modified polysiloxanes, alkyl-modified polysiloxanes, and fluorine-modified polysiloxanes; polyols such as polyethylene glycol, glycerol, 1,3-butanediol, erythritol, sorbitol, xylitol, maltitol, propylene glycol, dipropylene glycol, diglycerol, isoprene glycol, 1,2-pentanediol, 2,4-hexanediol, 1,2-hexanediol, and 1,2-octanediol; moisturizing components such as lactic acid and sodium lactate; powders such as mica, talc, kaolin, synthetic mica, calcium carbonate, magnesium carbonate, silicic anhydride (silica), aluminum oxide, and barium sulfate, which are optionally surface-treated; inorganic pigments such as red iron oxide, yellow iron oxide, black iron oxide, cobalt oxide, ultramarine, prussian blue, titanium oxide, and zinc oxide, which are optionally surface-treated; pearls such as titanium mica, fish scale foil, and bismuth oxychloride, which are optionally surface-treated; organic dyes such as Red No. 202, Red No. 228, Red No. 226, Yellow No. 4, Blue No. 404, Yellow No. 5, Red No. 505, Red No. 230, Red No. 223, Orange No. 201, Red No. 213, Yellow No. 204, Yellow No. 203, Blue No. 1, Green No. 201, Violet No. 201, and Red No. 204, which may be lake dyes; organic powders such as polyethylene powders, poly(methyl methacrylate), nylon powders, and organopolysiloxane elastomers; ultraviolet absorbers such as para-aminobenzoic acid-based ultraviolet absorbers, anthranilic acid-based ultraviolet absorbers, salicylic acid-based ultraviolet absorbers, cinnamic acid-based ultraviolet absorbers, benzophenone-based ultraviolet absorbers, sugar-based ultraviolet absorbers, 2-(2'-hydroxy-5'-t-octylphenyl) benzotriazole, and 4-methoxy-4'-t-butyldibenzoylmethane; lower alcohols such as ethanol and isopropanol; antimicrobial agents such as phenoxyethanol; antiseptics such as methylparaben; bases such as macrogol; pH adjusters such as sodium hydroxide; plasticizers; and solvents such as crotamiton and benzyl alcohol.

Examples of especially preferred components include esters of medium chain fatty acids, such as medium-chain triglyceride; esters of dibasic acids which do not belong to diester carbonate, such as diethyl adipate, diisopropyl adipate, and diethyl sebacate; and plasticizers such as triethyl citrate, diethylene glycol monoethyl ether, and capric acid monoglyceride. These increase solubility of the effective component. The content of each of these components is preferably 1 to 15% by mass with respect to the total amount of the composition for external use.

Further preferred examples of the solvent include alcohols. The alcohol is preferably the combination of ethanol and a polyol. The content ratio (mass ratio) between these is preferably 1:4 to 4:1.

Preferred examples of the polyol include 1,3-butanediol, isoprene glycol (3-methyl-1,3-butanediol), 1,2-pentanediol, polyethylene glycol, propylene glycol, polypropylene glycol, and glycerol. The content of the alcohol is preferably not less than 10% by mass, especially preferably 20 to 60% by mass with respect to the total amount of the composition for external use. A mode in which glycerol is contained at not less than 15% by mass, more preferably at 20% by mass, is preferred. Usually, in cases where the content of the alcohol exceeds 10% by mass, especially in cases where the content of glycerol exceeds 15% by mass, foaming using a pump foamer is difficult. The present invention overcomes this problem by combination with a nonionic surfactant.

According to a conventional method, the essential component(s) and the arbitrary component(s) may be processed into a composition for external use in a solubilized form, and the resulting composition may be processed into a pharmaceutical by filling the composition into a pump foamer.

The pump foamer is not limited as long as it allows foaming of the composition in the solubilized form. Those normally employed for cosmetics and pharmaceuticals may be used. The pump foamer is preferably one which is used as an external pharmaceutical composition.

That is, the (pharmaceutical) composition for external use of the present invention is a composition for a (pharmaceutical) composition for external use in a foam state to be used with a pump foamer.

Since the thus obtained composition for external use is a solubilized formulation, the effective component is uniformly dissolved therein, and the composition can be used in the form of foam. Thus, the composition can be smoothly spread on the affected area without irritating the area, and the effective component can be uniformly distributed throughout the affected area. By such a mode, sufficient exertion of the effect of the effective component is possible.

EXAMPLES

The present invention is described below by way of Examples in more detail.

Example 1

According to the prescription described below, External Pharmaceutical Composition 1 of the present invention was prepared. That is, the prescribed components were heated at 80° C. with stirring for solubilization, and then allowed to cool to room temperature with stirring, to obtain External Pharmaceutical Composition 1 of the present invention. The composition was filled into a pump foamer (manufactured by Daiwa Can Company) to obtain External Pharmaceutical 1 of the present invention. This discharged a fine foam.

TABLE 1

| Component | Mass % |
| --- | --- |
| Maxacalcitol | 0.05 |
| Polyoxyethylene (10) lauryl ether | 1.5 |
| N-Methyl-2-pyrrolidone | 5 |
| Diisopropyl adipate | 1 |
| Lauric acid diethanolamide | 3.5 |
| Polyoxyethylene (60) hydrogenated castor oil | 2 |
| 1,3-Butanediol | 25 |
| Ethanol | 10 |
| Methylparaben | 0.3 |
| Water | Remainder |

Comparative Example 1

N-methyl-2-pyrrolidone in External Pharmaceutical Composition 1 was replaced with diisopropyl adipate to prepare Comparative External Pharmaceutical Composition 1. The composition was filled into a pump foamer, and discharged from the pump foamer. As a result, foam could be hardly found, and the composition was discharged as a liquid.

Example 2

According to the prescription described below, External Pharmaceutical Composition 2 was prepared in the same manner as in Example 1. The prepared composition was filled into a pump foamer to obtain External Pharmaceutical 2 of the present invention. This discharged a fine foam.

TABLE 2

| Component | Mass % |
| --- | --- |
| Tretinoin tocoferil | 0.05 |
| Polyoxyethylene (10) lauryl ether | 1.5 |
| N-Methyl-2-pyrrolidone | 3 |
| Ethylene carbonate | 2 |
| Diisopropyl adipate | 1 |
| Lauric acid diethanolamide | 3.5 |
| Polyoxyethylene (60) hydrogenated castor oil | 2 |
| 1,3-Butanediol | 25 |
| Ethanol | 10 |
| Methylparaben | 0.3 |
| Water | Remainder |

Example 3

According to the prescription described below, External Pharmaceutical Composition 3 was prepared in the same manner as in Example 1. The prepared composition was filled into a pump foamer to obtain External Pharmaceutical 3 of the present invention. This discharged a fine foam.

TABLE 3

| Component | Mass % |
| --- | --- |
| Terbinafine hydrochloride | 0.05 |
| Polyoxyethylene (10) lauryl ether | 1.5 |
| N-Methyl-2-pyrrolidone | 3 |
| Crotamiton | 2 |
| Diisopropyl adipate | 4 |
| Lauric acid diethanolamide | 3.5 |
| Polyoxyethylene (60) hydrogenated castor oil | 2 |
| 1,3-Butanediol | 25 |
| Ethanol | 10 |
| Methylparaben | 0.3 |
| Water | Remainder |

Example 4

According to the prescription described below, External Pharmaceutical Composition 4 was prepared in the same manner as in Example 1. The prepared composition was filled into a pump foamer to obtain External Pharmaceutical 4 of the present invention. This discharged a fine foam.

TABLE 4

| Component | Mass % |
| --- | --- |
| Tacrolimus | 0.1 |
| Polyoxyethylene (10) lauryl ether | 1.5 |
| N-Methyl-2-pyrrolidone | 5 |
| Diisopropyl adipate | 1 |
| Lauric acid diethanolamide | 3.5 |
| Polyoxyethylene (60) hydrogenated castor oil | 2 |
| 1,3-Butanediol | 25 |
| Ethanol | 10 |
| Methylparaben | 0.3 |
| Water | Remainder |

Example 5

According to the prescription described below, External Pharmaceutical Composition 5 was prepared in the same manner as in Example 1. The prepared composition was filled into a pump foamer to obtain External Pharmaceutical 5 of the present invention. This discharged a fine foam.

TABLE 5

| Component | Mass % |
| --- | --- |
| Suprofen | 1 |
| Polyoxyethylene (10) lauryl ether | 1.5 |
| N-Methyl-2-pyrrolidone | 5 |
| Diisopropyl adipate | 1 |
| Lauric acid diethanolamide | 3.5 |
| Polyoxyethylene (60) hydrogenated castor oil | 2 |
| 1,3-Butanediol | 25 |
| Ethanol | 10 |
| Methylparaben | 0.3 |
| Water | Remainder |

Examples 6 to 10

According to the prescriptions described below, External Pharmaceutical Compositions 6 to 10, and External Pharmaceutical Compositions of Comparative Examples 2 and 3 were prepared in the same manner as in Example 1. Each composition was filled into a pump foamer to obtain External Pharmaceuticals 6 to 10 of the present invention and External Pharmaceuticals of Comparative Examples 2 and 3. In Table 6, the content of each prescribed component is represented as mass % with respect to the total amount of the external pharmaceutical composition. The external pharmaceuticals of the present invention discharged fine foams. External Pharmaceutical of Comparative Example 2 could not be uniformly solubilized. External pharmaceuticals of Comparative Examples 2 and 3 hardly produced foams, and were discharged as liquids.

TABLE 6

| Component name | External pharmaceutical composition 6 | External pharmaceutical composition 7 | External pharmaceutical composition 8 | External pharmaceutical composition 9 | External pharmaceutical composition 10 | Comparative Example 2 | Comparative Example 3 |
|---|---|---|---|---|---|---|---|
| Betamethasone butyrate propionate | 0.05 | 0.05 | 0.05 | 0.05 | 0.05 | 0.05 | 0.05 |
| N-Methyl-2-pyrrolidone | 6 | 6 | 6 | 6 | | | |
| Propylene carbonate | | | | | 6 | | |
| Crotamiton | | | | | | 6 | |
| Benzyl alcohol | | | | | | | 6 |
| Diisopropyl adipate | 1 | | | | | | |
| 1,3-Butanediol | 30 | 15 | 15 | 10 | 15 | 15 | 15 |
| Macrogol 400 | | 2.5 | 2.5 | 3.5 | 2.5 | 2.5 | 2.5 |
| Ethanol | 10 | | | | | | |
| Polyoxyethylene (10) lauryl ether | 2 | 2 | 1.5 | 1.5 | 1.5 | 1.5 | 1.5 |
| Lauric acid diethanolamide | 2 | | | | | | |
| Polyethylene (40) glycol monostearate | | 2 | 1.5 | 1.5 | 1.5 | 1.5 | 1.5 |
| Polyoxyethylene (60) hydrogenated castor oil | 2 | 2 | 1.5 | 1.5 | 1.5 | 1.5 | 1.5 |
| D-Sorbitol | | 0.25 | 0.25 | 0.25 | 0.25 | 0.25 | 0.25 |
| Sodium hydroxide | | | Appropriate amount | Appropriate amount | | | |
| Water | 46.95 | 70.2 | 71.7 | 75.7 | 71.7 | 71.7 | 71.7 |
| Total | 100 | 100 | 100 | 100 | 100 | 100 | 100 |

Examples 11 and 12

According to the prescriptions described below, External Pharmaceutical Compositions 11 and 12 were prepared. That is, the components of (A), the components of (B), the components of (C), and the components of (D) were separately mixed and dissolved under heat at 80° C., followed by allowing the resulting mixtures to cool to room temperature. The mixture of (B), the mixture of (C), and the mixture of (D) were sequentially added to the mixture of (A), to obtain External Pharmaceutical Compositions 11 and 12 of the present invention. Each of External Pharmaceutical Compositions 11 and 12 was filled into a pump foamer to obtain External Pharmaceuticals 11 and 12 of the present invention. In Table 7, the content of each prescribed component is represented as mass % with respect to the total amount of the external pharmaceutical composition. The external pharmaceuticals of the present invention discharged fine foams.

TABLE 7

| | Component name | External pharmaceutical composition 11 | External pharmaceutical composition 12 |
|---|---|---|---|
| (A) | N-Methyl-2-pyrrolidone | 3 | 3 |
| | 1,3-Butanediol | 15 | 15 |
| | Polyoxyethylene (9) lauryl ether | 2 | 2 |
| | Polyethylene (40) glycol monostearate | 1 | 1 |
| | Polyoxyethylene (60) hydrogenated castor oil | 1 | 1 |
| | Glycerol | 15 | 25 |
| (B) | D-Sorbitol | 0.5 | 0.5 |
| | Water | 17.675 | 12.675 |
| (C) | Sodium hyaluronate | 0.025 | 0.025 |
| | Water | 40 | 35 |
| (D) | Heparinoid | 0.3 | 0.3 |
| | Water | 5 | 5 |
| | Total | 100 | 100 |

Example 13

<Test Method>

In each of 200-mL tall glass beakers, 100 g of External Pharmaceutical Composition 8 or 10 of Example 8 or 10, or External Pharmaceutical Composition of Comparative Example 2 or 3 was placed, and each composition was stirred with a homomixer at 3000 rpm for 1 minute to allow foaming. Thereafter, the composition was left to stand for 2 minutes until the border between the foam and the solution became clear. The height of the foam was measured using a caliper. The results are shown in Table 8.

External Pharmaceutical Compositions 8 and 10 produced high-height foams, and showed favorable foaming. On the other hand, External Pharmaceutical Compositions of Comparative Examples 2 and 3 produced low-height foams, and showed poor foaming.

TABLE 8

| External pharmaceutical composition | Foam height (mm) |
|---|---|
| External pharmaceutical composition 8 | 39.03 |
| External pharmaceutical composition 10 | 38.76 |
| Comparative Example 2 | 6.95 |
| Comparative Example 3 | 12.51 |

Examples 14 to 18

According to the prescriptions described below, External Pharmaceutical Compositions 14 to 18, and External Pharmaceutical Compositions of Comparative Examples 4 and 5 were prepared in the same manner as in Example 1. Each composition was filled into a pump foamer to obtain External Pharmaceuticals 14 to 18 of the present invention and External Pharmaceuticals of Comparative Examples 4 and 5. In Table 9, the content of each prescribed component is represented as mass % with respect to the total amount of the external pharmaceutical composition. External Pharmaceuticals 14 to 18 of the present invention discharged fine foams. External Pharmaceuticals of Comparative Examples 4 and 5 showed poor foaming, and discharged the compositions as liquids with low foam-forming ability.

TABLE 9

| Component name | External pharmaceutical composition 14 | External pharmaceutical composition 15 | External pharmaceutical composition 16 | External pharmaceutical composition 17 | External pharmaceutical composition 18 | Comparative Example 4 | Comparative Example 5 |
|---|---|---|---|---|---|---|---|
| Mometasone furancarboxylate | 0.1 | | 0.1 | | | 0.1 | |
| Dexamethasone valerate | | 0.12 | | 0.12 | | | 0.12 |
| Hydrocortisone | | | | | 0.1 | | |
| N-Methyl-2-pyrrolidone | 6 | 6 | | | | | |
| Propylene carbonate | | | 6 | 6 | 6 | | |
| Benzyl alcohol | | | | | | 6 | 6 |
| 1,3-Butanediol | 15 | 15 | 15 | 15 | 15 | 15 | 15 |
| Macrogol 400 | 2.5 | 2.5 | 2.5 | 2.5 | 2.5 | 2.5 | 2.5 |
| Polyoxyethylene (10) lauryl ether | 1.5 | 1.5 | 1.5 | 1.5 | 1.5 | 1.5 | 1.5 |
| Polyethylene (40) glycol monostearate | 1.5 | 1.5 | 1.5 | 1.5 | 1.5 | 1.5 | 1.5 |
| Polyoxyethylene (60) hydrogenated castor oil | 1.5 | 1.5 | 1.5 | 1.5 | 1.5 | 1.5 | 1.5 |
| D-Sorbitol | 0.25 | 0.25 | 0.25 | 0.25 | 0.25 | 0.25 | 0.25 |
| Water | 71.65 | 71.63 | 71.65 | 71.63 | 71.65 | 71.65 | 71.63 |
| Total | 100 | 100 | 100 | 100 | 100 | 100 | 100 |

Example 19

<Test Method>

For each of External Pharmaceutical Compositions 14 to 17 and External Pharmaceutical Compositions of Comparative Examples 4 and 5, the height of the foam was measured according to the method described in the test method for Example 13. The results are shown in Table 10. External Pharmaceutical Compositions 14 to 17 produced high-height foams, and showed favorable foaming. On the other hand, External Pharmaceutical Compositions of Comparative Examples 4 and 5 produced low-height foams, and showed poor foaming.

TABLE 10

| External pharmaceutical composition | Foam height (mm) |
|---|---|
| External pharmaceutical composition 14 | 30.70 |
| External pharmaceutical composition 15 | 40.53 |
| External pharmaceutical composition 16 | 35.61 |
| External pharmaceutical composition 17 | 40.24 |
| Comparative Example 4 | 26.21 |
| Comparative Example 5 | 23.77 |

Examples 20 to 22

According to the prescriptions described below, Compositions for External Use 20 to 22 were prepared in the same manner as in Example 1. Each composition was filled into a pump foamer to obtain External Preparations 20 to 22 of the present invention. The external preparations of the present invention discharged fine foams.

TABLE 11

| Component | Mass % |
|---|---|
| N-Methyl-2-pyrrolidone | 6 |
| Diisopropyl adipate | 1 |
| 1,3-Butanediol | 30 |
| Ethanol | 10 |
| Lauromacrogol | 2 |
| Lauric acid diethanolamide | 2 |
| Polyoxyethylene (60) hydrogenated castor oil | 2 |
| Water | Remainder |

TABLE 12

| Component | Mass % |
|---|---|
| N-Methyl-2-pyrrolidone | 6 |
| 1,3-Butanediol | 15 |
| Macrogol 400 | 2.5 |
| Lauromacrogol | 2 |
| Polyethylene (40) glycol monostearate | 2 |
| Polyoxyethylene (60) hydrogenated castor oil | 2 |
| D-Sorbitol | 0.25 |
| Water | Remainder |

TABLE 13

| Component | Mass % |
|---|---|
| N-Methyl-2-pyrrolidone | 6 |
| 1,3-Butanediol | 15 |
| Macrogol 400 | 2.5 |
| Sodium N-acyl-L-glutamate | 0.05 |
| Lauric acid diethanolamide | 1.5 |
| Polyoxyethylene (60) hydrogenated castor oil | 0.5 |
| D-Sorbitol | 0.25 |
| Lactic acid | 0.05 |
| Water | Remainder |

INDUSTRIAL APPLICABILITY

The present invention can be applied to pharmaceuticals.

What is claimed is:

1. A composition for external use comprising:
    1) an N-alkyl-2-pyrrolidone;
    2) at least one nonionic surfactant; and
    3) not less than 15% by mass of glycerol with respect to a total amount of the composition for external use,
    wherein said composition is in a foam state upon use with a pump foamer,
    wherein said N-alkyl-2-pyrrolidone comprises one or more selected from the group consisting of N-methyl-2-pyrrolidone, N-ethyl-2-pyrrolidone, N-propyl-2-pyrrolidone, and N-butyl-2-pyrrolidone,
    wherein said at least one noionic surfactant comprises a combination of: a) a polyoxyethylene (average addition molar number is 6 to 10) fatty acid (average carbon number is 6 to 14) monoglyceride and/or a fatty acid diethanol amide; and b) a polyoxyethylene (average addition molar number is 8 to 25) alkyl ether and/or a polyoxyethylene (average addition molar number is 20 to 80) hydrogenated castor oil, wherein said composition does not comprise a surfactant other than the noionic surfactant, and wherein said composition does not comprise a foam-forming gas.

2. The composition for external use according to claim 1, further comprising:

4) a pharmaceutically-effective component.

3. The composition for external use according to claim 2, wherein said pharmaceutically-effective component comprises one or more selected from the group consisting of vitamin A and derivatives thereof, vitamin D and derivatives thereof, vitamin E and derivatives thereof, immunosuppressants, antibiotics, antifungal agents, anti-inflammatory agents, glucocorticoid, heparin, and heparinoids.

4. A pharmaceutical prepared by filling the composition for external use according to claim 2 in a pump foamer.

5. A method of preparing a pharmaceutical composition comprising filling a pump foamer with the composition of claim 2.

6. The composition for external use according to claim 1, comprising a combination of ethanol and polyol at a content mass ratio between 1:4 to 4:1 as an alcohol.

7. The composition for external use according to claim 1, wherein the surfactant comprises lauromacrogol.

8. The composition for external use according to claim 1, wherein the composition is for avoiding an irritation due to foam-forming gas and for use under conditions where no washing operation is carried out.

9. A composition for external use consisting essentially of:

1) an N-alkyl-2-pyrrolidone;
2) surfactants;
3) not less than 15% by mass of glycerol with respect to a total amount of the composition for external use, and
4) a pharmaceutically-effective component, wherein said composition does not comprise ionic surfactants and propellants, wherein said N-alkyl-2-pyrrolidone comprises one or more selected from the group consisting of N-methyl-2-pyrrolidone, N-ethyl-2-pyrrolidone, N-propyl-2-pyrrolidone, and N-butyl-2-pyrrolidone, wherein the surfactants comprise a combination of: a) a polyoxyethylene (average addition molar number is 6 to 10) fatty acid (average carbon number is 6 to 14) monoglyceride and/or a fatty acid diethanol amide; and b) a polyoxyethylene (average addition molar number is 8 to 25) alkyl ether and/or a polyoxyethylene (average addition molar number is 20 to 80) hydrogenated castor oil, wherein all of the surfactants in the composition are nonionic surfactants, and wherein said composition is in a foam state upon use with a pump foamer.

10. The composition for external use according to claim 9, wherein the composition does not comprise a pharmaceutically-effective component.

11. The composition for external use according to claim 9, wherein said pharmaceutically-effective component comprises one or more selected from the group consisting of vitamin A and derivatives thereof, vitamin D and derivatives thereof, vitamin E and derivatives thereof, immunosuppressants, antibiotics, antifungal agents, anti-inflammatory agents, glucocorticoid, heparin, and heparinoids.

* * * * *